US008460676B2

(12) United States Patent
Graf et al.

(10) Patent No.: US 8,460,676 B2
(45) Date of Patent: *Jun. 11, 2013

(54) COMPOSITION COMPRISING VLP AND AMYLOID BETA PEPTIDE

(75) Inventors: Ana Graf, Riehen (CH); Matthias Staufenbiel, Lörrach (DE); Thomas Blättler, Böckten (CH); Paolo Paganetti, Basel (CH)

(73) Assignee: Novartis AG, Basel (CH)

( * ) Notice: Subject to any disclaimer, the term of this patent is extended or adjusted under 35 U.S.C. 154(b) by 174 days.

This patent is subject to a terminal disclaimer.

(21) Appl. No.: 12/971,534

(22) Filed: Dec. 17, 2010

(65) Prior Publication Data

US 2011/0086036 A1    Apr. 14, 2011

Related U.S. Application Data

(62) Division of application No. 11/718,665, filed as application No. PCT/EP2005/011788 on Nov. 3, 2005, now Pat. No. 7,867,499.

(30) Foreign Application Priority Data

Nov. 5, 2004    (GB) .................................. 0424563.5

(51) Int. Cl.
| A61K 39/295 | (2006.01) |
| A61K 38/00 | (2006.01) |
| A61K 39/385 | (2006.01) |
| A61K 39/12 | (2006.01) |
| A61K 35/76 | (2006.01) |
| G01N 33/6896 | (2006.01) |
| G01N 33/554 | (2006.01) |
| G01N 33/569 | (2006.01) |
| C12Q 1/68 | (2006.01) |
| C12Q 1/70 | (2006.01) |

(52) U.S. Cl.
USPC .................. 424/193.1; 424/281.1; 424/204.1; 424/158.1; 424/192.1; 424/196.11; 435/235.1; 514/17.8; 530/324; 530/403

(58) Field of Classification Search
None
See application file for complete search history.

(56) References Cited

U.S. PATENT DOCUMENTS

| 4,722,840 | A | 2/1988 | Valenzuela et al. |
| 4,959,314 | A | 9/1990 | Mark et al. |
| 5,143,726 | A | 9/1992 | Thornton et al. |
| 5,508,167 | A | 4/1996 | Roses et al. |
| 5,565,548 | A | 10/1996 | Neurath et al. |
| 5,698,424 | A | 12/1997 | Mastico et al. |
| 5,916,818 | A | 6/1999 | Irsch et al. |
| 5,928,647 | A | 7/1999 | Rock |
| 5,935,821 | A | 8/1999 | Chatterjee et al. |
| 6,004,763 | A | 12/1999 | Gengoux et al. |
| 6,054,312 | A | 4/2000 | Larocca et al. |
| 6,180,771 | B1 | 1/2001 | Thomas et al. |
| 6,231,864 | B1 | 5/2001 | Birkett |
| 6,380,364 | B1 | 4/2002 | Mueller et al. |
| 6,743,427 | B1 | 6/2004 | Schenk |
| 6,827,937 | B2 | 12/2004 | Murray |
| 6,919,075 | B1 | 7/2005 | Solomon et al. |
| 6,932,971 | B2 | 8/2005 | Bachmann et al. |
| 6,964,769 | B2 | 11/2005 | Sebbel et al. |
| 7,115,266 | B2 | 10/2006 | Bachmann |
| 7,128,911 | B2 | 10/2006 | Bachmann et al. |
| 7,264,810 | B2 | 9/2007 | Renner et al. |
| 7,279,165 | B2 | 10/2007 | Bachmann et al. |
| 7,320,793 | B2 | 1/2008 | Renner et al. |
| 7,867,499 | B2 * | 1/2011 | Graf et al. .................. 424/193.1 |
| 2002/0052311 | A1 | 5/2002 | Solomon et al. |
| 2002/0064533 | A1 | 5/2002 | Murray |
| 2002/0081295 | A1 | 6/2002 | Schiller et al. |
| 2003/0073655 | A1 | 4/2003 | Chain |
| 2003/0157117 | A1 | 8/2003 | Rasmussen et al. |
| 2003/0157479 | A1 | 8/2003 | Bachmann et al. |
| 2003/0175290 | A1 | 9/2003 | Renner et al. |
| 2003/0175711 | A1 | 9/2003 | Renner et al. |
| 2003/0219459 | A1 | 11/2003 | Bachmann et al. |
| 2004/0076611 | A1 | 4/2004 | Bachmann et al. |
| 2004/0076645 | A1 | 4/2004 | Bachmann et al. |
| 2004/0136993 | A1 | 7/2004 | Schenk |

FOREIGN PATENT DOCUMENTS

| EP | 0 038 154 A1 | 10/1981 |
| EP | 0 578 293 A1 | 1/1994 |
| EP | 0 385 610 B1 | 3/1994 |
| EP | 0 465 081 B1 | 4/1994 |
| EP | 0 283 505 B1 | 7/1994 |
| EP | WO2004/016282 | * 2/2004 |

(Continued)

OTHER PUBLICATIONS

Adhin, M.R., et al., "Nucleotide Sequence from the ssRNA Bacteriophage JP34 Resolves the Discrepancy between Serological and Biophysical Classification," Virology 170(1):238-242, Academic Press, Inc. (1989).

Ansel, K.M., et al., "A chemokine-driven positive feedback loop organizes lymphoid follicles," Nature 406(6793):309-314, Nature Publishing Group (2000).

Ansel, K.M., et al., "In Vivo-activated CD4 T Cells Upregulate CXC Cheomkine Receptor 5 and Reprogram Their Response to Lymphoid Chemokines," J. Exp. Med. 190(8):1123-1134, The Rockefeller University Press (1999).

Bachmann, M.F., and Zinkernagel, R.M., "The influence of virus structure on antibody responses and virus serotype formation," Immunology Today 17(12):553-558, Elsevier Science Ltd. (1996).

(Continued)

Primary Examiner — Jeffrey Stucker
Assistant Examiner — Aurora M Fontainhas
(74) Attorney, Agent, or Firm — Andrew K. Holmes

(57) ABSTRACT

The present invention relates to uses of a construct consisting of virus-like particle (VLP) structure chemically coupled to a fragment of the Aβ-1-42 peptide and its pharmaceutically acceptable salts (hereinafter CONSTRUCT), in particular to dosage regimens, modes of and dosage forms for the administration of a CONSTRUCT for the treatment of patients suffering from dementia, in particular dementia of the Alzheimer's type.

10 Claims, No Drawings

FOREIGN PATENT DOCUMENTS

| | | |
|---|---|---|
| EP | 1 541 140 | 6/2005 |
| JP | 09202735 A | 8/1997 |
| WO | 90/15878 A1 | 12/1990 |
| WO | 94/15585 A1 | 7/1994 |
| WO | 98/28624 A1 | 7/1998 |
| WO | 98/40100 A1 | 9/1998 |
| WO | 98/44955 | 10/1998 |
| WO | 99/27944 | 6/1999 |
| WO | 99/27949 | 6/1999 |
| WO | 99/28478 A1 | 6/1999 |
| WO | 99/40934 A1 | 8/1999 |
| WO | 99/57289 A2 | 11/1999 |
| WO | 00/23955 A1 | 4/2000 |
| WO | 00/32227 A2 | 6/2000 |
| WO | 00/50461 A1 | 8/2000 |
| WO | 01/18169 | 3/2001 |
| WO | 01/53457 A2 | 7/2001 |
| WO | 01/62284 A2 | 8/2001 |
| WO | 01/85208 A2 | 11/2001 |
| WO | 01/53457 A3 | 4/2002 |
| WO | 02/056905 A2 | 7/2002 |
| WO | 02/056907 A2 | 7/2002 |
| WO | 03/024480 A2 | 3/2003 |
| WO | WO 2004/016282 | 2/2004 |

OTHER PUBLICATIONS

Bachmann, M.F., and Zinkernagel, R.M., "Neutralizing Antiviral B Cell Responses," Annu. Rev. Immunol. 15:235-270, Annual Reviews, Inc. (1997).

Bachmann, M.F., et al., "Dendritic cells process exogenous viral proteins and virus-like particles for class I presentation to CD8+ cytotoxic T lymphocytes," Eur. J. Immunol. 26(11):2595-2600, VCH Verlagsgesellschaft mbH (1996).

Bachmann, M.F., et al., "TRANCE, a Tumor Necrosis Factor Family Member Critical for CD40 Ligand-independent T Helper Cell Activation," J. Exp. Med. 189(7):1025-1031, The Rockefeller University Press (1999).

Bard, F. et al., "Peripherally administered antibodies against amyloid .beta.-peptide enter the central nervous system and reduce pathology in a mouse model of Alzheimer disease," Nat. Med. 6(8):916-919, Nature Publishing Company (2000).

Bass, S., and Yang, M., "Expressing cloned genes in *Escherichia coli*," in Protein Function: A Practical Approach, 2nd ed., Creighton, T.E., ed., IRL Press, Oxford, Great Britain, 175:29-55, (1997).

Bowie, J.U., et al., "Deciphering the message in protein sequences: tolerance to amino acid substitutions.," Science 247(4948):1306-1310, (1990).

Brown, W.L., et al., "RNA bacteriophage capsid-mediated drug delivery and epitope presentation.," Intervirology 45(4-6):371-380, S. Karger AG Basel (2002).

Cesareni, G., "Peptide display on filamentous phage capsids: A new powerful tool to study protein-ligand interaction," FEBS Lett. 307(1):66-70, Elsevier Science Publishers B.V. (1992).

Chackerian, B., et al., "Induction of autoantibodies to mouse CCR5 with recombinant Papillomavirus particles," Proc Natl. Acad. Sci USA 96(5):2373-2378, (1999).

Crameri, R. and Suter, M., "Display of biologically active proteins on the surface of filamentous phages: a cDNA cloning system for selection of functional gene products linked to the genetic information responsible for their production," Gene 137(1):69-75, Elsevier Science Publishers B.V. (1993).

de la Cruz, V.F., et al., "Immunogenicity and Epitope Mapping of Foreign Sequences via Genetically Engineered Filamentous Phage," J. Biol. Chem. 263:4318-4322, The American Society for Biochemistry and Molecular Biology, Inc. (1988).

Dodart, J.-C., et al., "Immunotherapy for Alzheimer's disease: will vaccination work?," TRENDS in Molecular Medicine 9(3):85-87, (2003).

Donnelly, J.J., et al., "DNA Vaccines," Annu. Rev. Immunol. 15:617-648, Annual Reviews, Inc. (1997).

Fehr, T., et al., "T cell-Independent type I antibody response against B cell epitopes expressed repetitively on recombinant virus particles," Proc. Natl. Acad. Sci 95(16):9477-9481, (1998).

Fehr, T., et al., "Role of Repetitive Antigen Patterns for Induction of Antibodies Against Antibodies," J Exp Med. 185(10):1785-1792, The Rockefeller University Press (1997).

Frenkel, D., et al., "N-terminal EFRH sequence of Alzheimer's beta-amyloid peptide represents the epitope of its anti-aggregating antibodies," J.Neuroimmunol. 88:85-90 (1998).

Frenkel, D., et al., "High affinity binding of monoclonal antibodies to the sequential epitope EFRH of beta-amyloid peptide is essential for modulation of fibrillar aggregation," J.Neuroimmunol. 95:136-142 (1999).

Frenkel, D., et al., "Immunization against Alzheimer's beta -amyloid plaques via EFRH phage administration," PNAS 97(21):11455-11459, (2000).

Frenkel, D., et al., "Generation of auto-antibodies towards Alzheimer's disease vaccination," Vaccine 19(17-19):2615-2619, Elsevier Science, Ltd. (2001).

Frolov, I., et al., "Alphavirus-based expression vectors: strategies and applications," Proc. Natl. Acad. Sci 93(21):11371-11377, (1996).

Games et al. "Alzheimer-type neuropathology in transgenic mice over-expressing V717F beta-amyloid precursor protein," A letter in Nature, Feb. 9, 1995, 373:523-527.

Gilman, S., et al., "Clinical effects of Abeta immunization (AN1792) in patients with AD in an interrupted trial," Neurology 64(9):1553-1562, (2005).

Golmohammadi, R., et al., "The crystal structure of bacteriophage Q.beta. at 3.5.ANG. resolution," Structure 4(5):543-554, Current Biology, Ltd. (1996).

Harris, S.J., et al., "Prediction of murine MHC class I epitopes in a major house dust mite allergen and induction of T1-type CD8+ T cell responses," International Immunology 9(2):273-280, (1997).

Hedrick, J.A., and Zlotnik, A., "Identification and Characterization of a Novel β Chemokine Containing Six Conserved Cysteines," J. Immunol. 159(4):1589-1593, The American Association of Immunologists (1997).

Hilleman, M.R., "Six decades of vaccine development—a personal history," Nat. Med. Vaccine Suppl. 4(5 Suppl):507-514, (1998).

Holtzman, D.M., et al., "Abeta immunization and anti-Abeta antibodies: potential therapies for the prevention and treatment of Alzheimer's disease," Advanced Durg Delivery Reviews 54(12):1603-1613, Elsevier Science (2002).

Iannolo, G., et al., "Construction Exploitation and Evolution of a New Peptide Library Displayed at High Density by Fusion to the Major Coat Protein of Filamentous Phage," Biol. Chem. 378(6):517-521, Walter de Gruyter & Co. (1997).

Iannolo, G., et al., "Modifying Filamentous Phage Capsid: Limits in the Size of the Major Capsid Protein," J. Mol. Biol. 248(4):835-844, Academic Press, Ltd. (1995).

Janus, C., et al., "Aβ Peptide Immunization Reduced Behavioural Impairment and Plaques in a Model of Alzheimer's Disease," Nature 408:979-982 (2000).

Janus, C., "Vaccines for Alzheimer's disease: how close are we?," CNS Drugs 17(7):457-474, Adis Data Information (2003).

Jegerlehner, A., et al., "A molecular assembly system that renders antigens of choise highly repetitive for induction of protective B cell responses," Vaccine 20(25-26):3104-3112, Elsevier Science, Ltd. (2002).

Johnson-Wood, K., et al. (1997) Proc. Natl. Acad. Sci. USA 94:1550-1555, 1997.

Kastelein, R.A. et al., "Effect of the sequence upstream from the ribosome-binding site on the yield of protein from the cloned gene for phage MS2 coat protein," Gene 23(3):245-254, Elsevier (1983).

Klovins, J., et al., "Nucleotide sequence of a ssRNA phage from Acinetobacter: kinship to coliphages," Journal of general Virology 83(Pt 6):1523-1533, SGM (2002).

Kovacsovics-Bankowski, M., et al., "Efficient major histocompatibility complex class I presentation of exogenous antigen upon phagocytosis by macrophages," Proc. Natl. Acad. Sci. USA 90:4942-4946, National Academy Press (1993).

Kozlovska, T.M., et al., "Recombinant RNA phage Q.beta. capsid particles synthesized and self-assembled in *Escherichia coli*," Gene 137(1):133-137, Elsevier Science Publishers B.V. (1993).

Kozlovska, T.M., et al., "RNA Phage Q.beta. Coat Protein as a Carrier for Foreign Epitopes," Intervirology 39(1-2):9-15, S. Karger AG (1996).

Kozlovskaya, T.M., et al., "Formation of capsid-like structures as a result of the expression of a cloned envelope protein gene from RNA-containing bacteriophage," Dokl. Akad. Nauk. SSSR 287:452-455, Erivan Akademiia Nauk Armianskol Ssr (1986).

Kratz, P.A., et al., "Native display of complete foreign protein domains on the surface of hepatitis B virus capsids," Proc. Natl. Acad. Sci 96(5):1915-1920, (1999).

Lechner, F., et al. "Virus-like particles as a modular system for novel vaccines," Intervirology 45(4-6):212-217, S. Karger AG Basel (2002).

Lim, F., et al., "The RNA-binding Site of Bacteriophage Q.beta. Coat Protein," J. Biol. Chem. 271(50):31839-31845, The American Society for Biochemistry and Molecular Biology, Inc. (1996).

Loktev, V.B., et al., "Design of Immunogens as components of a new generation of molecular vaccines," J. Biotechnol. 44(1-3):129-37, Elsevier Science (1996).

Lo-Man, R., et al., "A recombinant virus-like particle system derived from parvovirus as an efficient antigen carrier to elicit a polarized Th1 immune response without adjuvant," Eur. J. Immunol. 28(4):1401-1407, Wiley-VCH Verlag GmbH (1998).

McGeer, P.L., McGeer, E., "Is there a future for vaccination as a treatment for Alzheimer's disease?," Neurobiology of Aging 24(3):391-395, (2003).

Minenkova, O.O., et al., "Design of specific immunogens using filamentous phage as the carrier," Gene 128(1):85-88, Elsevier Science Publishers B.V. (1993).

Morgan, D., et al., "A beta peptide vaccination prevents memory loss in an animal model of Alzheimer's disease," Nature 408: 982-985 (2000).

NCBI Entrez GenBank Report, Accession No. AAA16663, Kozlovska, T. et al, "Recombinant RNA phage Q beta capsid particles synthesized and self assembled in *Esherichia coli*", Gene, 137(1), pp. 133-137, (1993).

NCBI Entrez GenBank Report, Accession No. AAC14699, Beekwilder, M.J., et al, "Secondary Structure Model for the last two domains of single-stranded RNA phage Q beta", J. Molecular Biology, 247 (5) pp. 903-917 (1995).

NCBI Entrez GenBank Report, Accession No. AAC14699, Beekwilder, M.J., et al, , "Secondary Structure Model for the first three domains of single-stranded RNA phage Q beta RNA control of protein synthesis", J. Molecular Biology, 256 (1) pp. 8-19 (1996).

NCBI Entrez GenBank Report, Accession No. AAC14704, Beekwilder, M.J., et al, "Secondary Structure Model for the last two domains of single-stranded RNA phage Q beta", J. Molecular Biology, 247 (5) pp. 903-917 (1995).

NCBI Entrez GenBank Report, Accession No. AAC14704, Beekwilder, M.J., et al, "Secondary Structure Model for the first three domains of single-stranded RNA phage Q beta RNA control of protein synthesis", J. Molecular Biology, 256 (1) pp. 8-19 (1996).

NCBI Entrez GenBank Report, Accession No. CAA30374, Inokuchi, Y. et al., "Analysis of the complete nucleotide sequence of the group IV RNA coliphage SP", Nucleic Acids Res., 16 (13) pp. 6205-6221 (1998).

NCBI Entrez GenBank Report, Accession No. NP040754, Inokuchi, Y., et al., "The complete nucleotide sequence of the group II RNA coliphage GA", J. Biochem, 99 (4), pp. 1169-1180, (1986).

NCBI Entrez GenBank Report, Accession No. P03611, Weber, K. et al., "Amino acid sequence of the F-2 coat protein", J. Biol. Chem., 242, pp. 3563-3578, (1967).

NCBI Entrez, GenBank Report, Accession No. VCBPM2, from Min Jou, W., et al. (Jan. 2001).

NCBI Entrez GenBank Report, Accession No. VCBPQB, Maita, T. et al, "The amino acid sequence of the Q coat protein", J. Biol. Chem. 246, (16), pp. 5003-5024 (1971).

Neurath, A.R., et al., "Hepatitis B Virus surface antigen (HBsAg) as carrier for synthetic peptides having an attached hydrophobic tail," Mol. Immunol. 26:53-62, Pergamon Press (1989).

Ni, C.-Z., et al., "Crystal structure of the coat protein from the GA bacteriophage: Model of the unassembled dimer," Protein Sci. 5:2485-2493, Cambridge University Press (1996).

Nicoll, James A.R., et al., "Neuropathology of human Alzheimer disease after immunization with amyloid- peptide: a case report," doi:10.1038/nm840, Nat. Med. 9: 448-452. (2003).

Nieland, J.D., et al., "Chimeric papillomavirus virus-like particles induce a murine self-antigen-specific protective and therapeutic anti-tumor immune response," Journal of Cellular Biochemistry 73(2):145-152, Wiley-Liss Inc. (1999).

Orgogozo, J-M, et al., "Meningoencephalitis in a subset of patients with Alzheimer's disease after Ab immunization" Neurology 61: 46-54 (2003).

Ormstad, H., et al., "Airborne house dust particles and diesel exhaust particles as allergen carriers.," Clinical and Experimental Allergy 28(6):702-708, Blackwell Science Ltd. (1998).

O'Shea, E.K., et al., "Evidence That the Leucine Zipper is a Coiled Coil," Science 243(4890):538-542, American Association for the Advancement of Science (1989).

O'Shea, E.K., et al., "Mechanism of Specificity in the Fos-Jun Oncoprotein Heterodimer," Cell 68(4):699-708, Cell Press (1992).

Pasek, M., et al., "Hepatitis B virus genes and their expression in *E. coli*," Nature 282(5739):575-578, Macmillan Journals Ltd. (1979).

Perham, R.N., et al., "Engineering a peptide epitope display system on filamentous bacteriophage," FEMS Microbiol. Rev. 17(1-2):25-31, Elsevier Science Publishers on behalf of the Federation of European Microbiological Societies (1995).

Petrenko, V.A., et al., "A library of organic landscapes on filamentous phage," Protein Engin. 9(9):797-801, Oxford University Press (1996).

Priano, C., et al., "A Complete Plasmid-based Complemenation System for RNA Coliphage Qβ: Three Proteins of Bacteriophages Qβ (Group III) and SP (Group IV) can be Interchanged," J. Mol. Biol. 249(2):283-297, Academic Press, Ltd. (1995).

Raychaudhuri, S., and Rock, K.L., "Fully mobilizing host defense: Building better vaccines," Nat. Biotechnol. 16(11):1025-1031, Nature America, Inc. (1998).

Robinson, C.R., and Sauer, R.T., "Optimizing the stability of single-chain proteins by linker length and composition mutagenesis," PNAS 95(11):5929-5934, National Academy of Science (1998).

Roesch, P.L., and Blomfield, I.C., "Leucine alters the interaction of the leucine-responsive regulatory protein (Lrp) with the fim switch to stimulate site-specific recombination in *Escherichia coli*," Mol. Microbiol. 27(4):751-761, Blackwell Science, Ltd. (1998).

Roher, A.E., et al., "Isolation and Chemical Characterization of Alzeheimer's Disease Paired Helical Filament Cytoskeletons: Differentiation from Amyloid Plaque Core Protein," J. Cell Biol. 107(6 Pt 2):2703-2716, The Rockefeller University Press (1988).

Roher, A.E., et al., "Morphological and Biochemical Analyses of Amyloid Plaque Core Proteins Purified from Alzheimer Disease Brain Tissue," J. Neurochem. 61(5):1916-1926, Raven Press, Ltd. (1993).

Romagnani, S., "The Th1/Th2 paradigm," Immunol. Today 18(6):263-266, Elsevier Science Ltd. (1997).

Schenk, D., et al., "Immunization with amyloid-β attenuates Alzheimer-disease-like pathology in the PDAPP mouse," Nature 400:173-177, Nature Publishing Group (1999).

Selkoe, D.J., "Translating cell biology into therapeutic advances in Alzheimer's disease," Nature 399(6738 Suppl):A23-A31, Nature Publishing Group (1999).

Sigurdson et al., Neurobiol. Aging 17 : 893-901 (1996).

Sigurdson et al., Neurobiol. Aging 18 : 591-608 (1997).

Solomon B., et al., "Monoclonal antibodies inhibit in vitro fibrillar aggregation of the Alzheimer beta-amyloid peptide," Proc. Natl. Acad. Sci. USA, Jan. 9; 93(1): 452-455 (1996).

Solomon, B., et al., "Disaggregation of Alzheimer beta-amyloid by site-directed mAb," Proc. Natl. Acad. Sci. USA, Apr. 15, 94(8): 4109-12 (1997).

Sturchler-Pierrat, C., et al., "Two amyloid precursor protein transgenic mouse models with Alzheimer disease-like pathology," Proc. Natl. Acad. Sci. USA 94(24):13287-13292, National Academy Press (1997).

Townsend, A., and Bodmer, H., "Antigen recognition by class I-restricted T lymphocytes," Ann. Rev. Immunol. 7:601-624, Annual Reviews, Inc. (1989).

Ulrich, R., et al., "Core particles of hepatitis B virus as carrier for foreign epitopes," Adv. Virus Res. 50:141-182, Academic Press (1998).

Vasiljeva, I., et al., "Mosaic Qβ coats as a new presentation model," FEBS Lett. 431(1):7-11, Federation of European Biochemical Societies (1998).

Walsh, D., et al., "Naturally secreted oligomers of amyloid bold beta protein potently inhibit hippocampal long-term potentiation in vivo," Nature 416: 535-539 (2002).

Willis, A.E., et al., "Immunological properties of foreign peptides in multiple display on a filamentous bacteriophage," Gene 128(1):79-83, Elsevier Science Publishers B.V. (1993).

Witherell, G.W., and Uhlenbeck, O.C., "Specific RNA Binding by Qβ Coat Protein," Biochemistry 28(1):71-76, American Chemical Society (1989).

Witte, L., et al., "Monoclonal antibodies targeting the VEGF receptor-2 (Flk1/KDR) as an anti-angiogenic therapeutic strategy," Cancer and Metastasis Reviews 17(2):155-161, Kluwer Academic Publishers (1998).

Wynne, S.A., et al., "The Crystal Structure of the Human Hepatitis B Virus Capsid," Mol. Cell 3(6):771-780, Cell Press (1999).

Yankner, B.A., et al., "Neurotoxicity of a fragment of the amyloid precursor associated with Alzheimer's disease," Science 245: 417-420 (1989).

Yeung, K., et al., "Suppression of Raf-1 kinase activity and MAP kinase signaling by RKIP," Nature 401:173-77 (1999).

Zhou, S., and Standring, D.N., "Cys Residues of the Hepatitis B Virus Capsid Protein Are Not Essential for the Assembly of Viral Core Particles but Can Influence Their Stability," J. Virol. 66(9):5393-5398, American Society for Microbiology (1992).

Geylis V et al., "P4-388 Human monoclonal antibodies against amyloid-beta (Abeta) engendered by EBV-immortalized lymphocytes from healthy adults", Neurobiology of Aging, vol. 25, p. S585, (2004).

Gaskin F et al., "Human Antibodies Reactive with Beta-Amyloid Protein in Alzheimer's Disease", Journal of Experimental Medicine, vol. 177, No. 4, pp. 1181-1186, (1993).

Xu S et al., "Increased Incidence of Anti-Beta-Amyloid Autoantibodies secreted Byepstein-Barr Virus Transformed B Cell Lines from Patients with Alzheimer's Disease", Mechanisms of Ageing and Development, Elsevier Sequoia, vol. 94, No. 1-3, pp. 213-222, (1997).

Golde Todd E, "Alzheimer disease therapy: Can the amyloid cascade be halted?", Journal of Clinical Investigation, vol. 111, No. 1, pp. 11-18, (2003).

Geylis V et al., "Human monoclonal antibodies against amyloid-beta from healthy adults", Neurobiology of Aging, vol. 26, No. 5, pp. 597-606, (2005).

Hock C et al., "Generation of antibodies specific for beta-amyloid by vaccination of patients with Alzheimer disease", Nature Medicine, Nature America, vol. 8, No. 11, pp. 1270-1275, (2002).

Du Yansheng et al., "Human anti-beta-amyloid antibodies block beta-amyloid fibril formation and prevent beta-amyloid-induced neurotoxicity", Brain, vol. 126, No. 9, pp. 1935-1939, (2003).

Li Qingyou et al., "Overcoming antigen masking of anti-amyloidbeta antibodies reveals breaking of B cell tolerance by virus-like particles in amyloidbeta immunized amyloid precursor protein transgenic mice", BMC Neuroscience, vol. 5, (2004).

Zamora et al., "Papillomavirus-like particle Aβ vaccine . . . " Biosis Accession No. PREV200400196099 & Soc. for Neuroscience Abstract Viewer & Itinerary Planner, Abstract No. 201.18, (2003).

NCBI Entrez GenBank Report, Accession No. P03612, Min Jou et al., "Nucleotide sequence of the gene coding for the bacteriophage MS2", Nature 237 (5350), pp. 82-88 (1972).

Hilleman, M., et al., "Six decades of vaccine development—a personal history"; Nature Medicine Vaccine Supplement, vol. 4., No. 5, pp. 507-514 (1998).

Traggiai, Elisabetta, et al., "An efficient method to make human monoclonal antibodies from memory B cells: potent neutralization of SARS coronavirus", Nature Medicine, 2004, vol. 10 (8), pp. 871-874.

Cujesov Ed. Prof V.I., g. Charkov, Iz-vo UkrFA, Industrial Technology of Pharmaceuticals, 1999, vol. 2, p. 662-677.

Geng T., Clinical Medication Journal, 2004, vol. 2, No. 1, pp. 28-31.

Maskovskij M.D., Lekarstvennye sredstva, M., Iz-vo Novaja Volna, 2001, vol. 1, p. 110-119, 388-392, 194, 199, 133-137.

Schupf, N., "Genetic and host factors for dementia in Down's syndrome", The British Journal of Psychiatry, vol. 180, pp. 405-410, 2002.

Weber Klaus et al., "Amino acid sequence of the F-2 coat protein", J. Biol. Chem., 242, pp. 3563-3578, 1967.

Min Jou W. et al., "Nucleotide sequence of the gene coding for the bacteriophage MS2", Nature 237 (5350), pp. 82-88, 1972.

Maita Tetsuo et al., "The amino acid sequence of the Q coat protein", J. Biol. Chem. 246, (16), pp. 5003-5024, 1971.

Staufenbiel et al., "Strong parenchymal amyloid reduction following CAD106 immunotherapy is associated with an increase in vascular Abeta but not microhemorrhages", Alzheimer's & Dementia: The Journal of the Alzheimer's Association, [vol. 5, Issue 4], 'Oral, O2-05: Therapeutics and Therapeutic Strategies: Immunotherapy', O2-05-06, p. P114, Jul. 2009.

Staufenbiel et al., "Immunization with Abeta1-6 Coupled to the Virus-Like Particle Qbeta (CAD106) Efficiently Removes beta-Amyloid Without Inducing Abeta-Reactive T-Cells," Alzheimer's & Dementia: The Journal of the Alzheimer's Association, 'Oral, O1-06: Therapeutic Strategies', O1-06-01, Abstract S20, Sunday, Jul. 16, 2006.

Winblad et al., "Results of the first-in-man study with active Abeta Immunotherapy CAD106 in Alzheimer patients", Alzheimer's & Dementia: The Journal of the Alzheimer's Association, [vol. 5, Issue 4], 'Oral, O2-05: Therapeutics and Therapeutic Strategies: Immunotherapy', O2-05-03, pp. P113-p114, Jul. 2009.

* cited by examiner

COMPOSITION COMPRISING VLP AND AMYLOID BETA PEPTIDE

The present invention relates to novel uses of a construct consisting of virus-like particle (VLP) structure chemically coupled to a fragment of the Aβ-1-42 peptide and its pharmaceutically acceptable salts (hereinafter CONSTRUCT), in particular to dosage regimens, modes of and dosage forms for the administration of a CONSTRUCT for the treatment of patients suffering from dementia, in particular dementia of the Alzheimer's type, especially mild to moderate or severe Alzheimer's Disease (AD), and vascular dementia with amyloid angiopathy to a method of isolating immune cells, especially antibody producing cells, and antibodies as well as there genes or fragments thereof generated by the immune system of a warm-blooded animal, especially a human, in response to the administration of the CONSTRUCT, the production of such antibodies and the pharmaceutical use of such antibodies.

The present invention relates to novel uses of a construct consisting of virus-like particle (VLP) structure chemically coupled to a fragment of the Aβ-1-42 peptide and its pharmaceutically acceptable salts (hereinafter CONSTRUCT), in particular to dosage regimens, modes of and dosage forms for the administration of a CONSTRUCT for the treatment of patients with increased AP-level, including but not limited to patients with dementia associated with Parkinson's disease, Lewy Body dementia.

The present invention also relates to novel uses of a construct consisting of virus-like particle (VLP) structure chemically coupled to a fragment of the Aβ-1-42 peptide and its pharmaceutically acceptable salts (hereinafter CONSTRUCT), in particular to dosage regimens, modes of and dosage forms for the administration of a CONSTRUCT for the prophylactic treatment of subjects at risk of developing AD, including but not limited to subjects with mild cognitive impairment, subjects with genotypes known to be associated with AD, such as ApoE4, subjects with Trisomy 21 and subjects with surrogate markers indicating risk for AD.

Considerable evidence has been accumulated suggesting that the β-amyloid peptide—the major component of senile amyloid plaques—plays a causal role in AD. Successful disease-modifying therapy for AD is likely to include products that affect the deposition of β-amyloid in the brain. Aβ-specific antibodies, actively generated by the immune system or passively administered, consistently reduce plaque burden in different transgenic mouse models for Aβ-amyloidosis. A first clinical attempt to stimulate the immune system of AD patients to generate Aβ-antibody, however, had to be suspended due to unacceptable side effects (meningoencephalitis in 6% of treated patients, Orgogozo J M, Gilman S, Dartigues J F, Laurent B, Puel M, Kirby L C, Jouanny P, Dubois B, Eisner L, Flitman S, Michel B F, Boada M, Frank F, Hock C (2003) Subacute meningoencephalitis in a subset of patients with AD after Aβ42 immunization. Neurology; 61: 46-54.).

Surprisingly, lesser adverse immune reactions and a lesser incidence of microhemorrhages are observed with the CONSTRUCTS disclosed herein. In particular, no adverse immune reaction nor increased incidence of microhemorrhages, is observed with CONSTRUCTS consisting of a VLP chemically coupled to the Aβ-1-6 peptide.

In a first aspect of the present invention, it was surprisingly found that the CONSTRUCT advantageously can be applied subcutaneously to warm-blooded animals, especially humans, suffering from dementia.

In another aspect of the present invention, it was surprisingly found that the CONSTRUCT advantageously can be applied intramuscularly, intranasally and orally to warm-blooded animals, especially humans, suffering from dementia.

In a second aspect, the present invention provides a dosage form for subcutaneous administration of the CONSTRUCT. The preferred dosage form for subcutaneous administration of the CONSTRUCT is an aqueous solution containing Phosphate Buffer Saline (PBS), between 0.25 and 0.75 mg/mL CONSTRUCT, preferably between 0.4 and 0.6 mg/mL, e.g. 0.5 mg/mL CONSTRUCT, and no further excipients. The dosage form can be kept frozen until shortly before usage. The dosage form is administered preferably by subcutaneous injection with a syringe to the warm-blooded animal, especially into the abdomen. For thawing of the dosage form, the dosage form can be kept at ambient temperature for about between 15 minutes and 45 minutes, e.g. 30 minutes. Preferably, before withdrawing drug substance, the vials are gently inverted several times for dispersion of potential sub-visual particles.

The CONSTRUCTS as employed in the present invention are known as such. For example, WO 00/3227 to Cytos discloses a technology for providing a construct comprising a core-particle (such as a VLP), a linker and an antigen, all together forming an ordered and repetitive antigen array. WO 02/056907 to Cytos and Novartis describes constructs comprising a VLP comprising recombinant proteins of a bacteriophage, such as Qβ, a linker and an antigen, e.g. Aβ1-42 or a fragment thereof, all together forming an ordered and repetitive antigen array. Preferably, a CONSTRUCT as used herein consists of capsid proteins of a RNA bacteriophage, more preferably of capsid proteins of the RNA bacteriophage Qβ, self-assembled into a highly ordered VLP structure chemically coupled with a bivalent linker to a fragment of the Aβ1-42 peptide, more preferably to Aβ-1-6. The CONSTRUCT can be prepared, purified and administered as disclosed in WO 00/3227, WO 02/056907 or WO2004/016282, especially in Example 13, which patent filings as well as the references cited therein are incorporated by reference into the present patent application, especially the end products of the Examples.

The term "treatment" as used herein relates in particular to a treatment aiming to halt pathogenic processes that lead to disease progression and/or has symptomatic effects.

The term "prophylactic treatment" as used herein relates in particular to a treatment aiming to halt pathogenic processes leading to disease.

The term "dementia of the Alzheimer's type" as used herein relates in particular to a disease as defined according to the Diagnostic and Statistical Manual of Mental Disorders, 4th edition (DSM-IV) criteria.

In a third aspect, the present invention relates to a method of treatment of dementia in human patients comprising administering 5 to 175 µg, preferably 15 to 125 µg, more preferably about 25 to 100 µg, e.g. 50 µg or 75 µg, of the CONSTRUCT to human patients in need thereof about every 4 to 8 weeks, preferably about every 5 to 7 weeks, in particular about every 6 weeks.

In a fourth aspect the present invention relates to a method of treatment of dementia in human patients comprising administering 5 to 1000 µg, preferably 5 to 300 µg, more preferably about 50 to 200, most preferably 50-150 µg, e.g. 50 µg or 75 µg, 100 µg, 125 µg, 150 µg of the CONSTRUCT to human patients in need thereof about every 4 to 8 weeks, preferably about every 5 to 7 weeks, in particular about every 6 weeks.

Frequency of injection can vary depending on the patient response.

For example the frequency of administration can vary if the injection has to be administered according to antibody titers.

The usefulness of the CONSTRUCTS in the treatment of the above-mentioned disorders can be confirmed in suitable clinical studies, e.g. those described in the Examples, e.g. applying a total daily dosage of 25 to 100 µg CONSTRUCT to patients every 4 to 8 weeks.

Suitable clinical studies are in particular randomized, double-blind, placebo-controlled, parallel studies in Alzheimer's patients or open label studies.

In a further aspect, the present invention pertains to a combination comprising at least one CONSTRUCT and at least one nootropic agent, preferably one cholinesterase-inhibitor, or memantine.

The term "nootropic agent" as used herein includes, but is not limited to nootropic plant extracts, calcium antagonists, cholinesterase inhibitors, dihydroergotoxin, nicergoline, piracetame, purine derivates, pyritinol, vincamine and vinpocetine.

The term "nootropic plant extracts" as used herein includes, but is not limited to extracts from Ginkgo leafs. The term "calcium antagonists" as used herein includes, but is not limited to cinnarizine and nimodipine. The term "cholinesterase inhibitors" as used herein includes, but is not limited to donepezil hydrochloride, rivastigmine and galantamine hydrobromide. The term "purine derivates" as used herein includes, but is not limited to pentifyllin.

Extracts from Ginkgo leafs can be administered, e.g., in the form as marketed, e.g. under the trademark Ginkodilat™ according to the information provided by the package insert. Cinnarizine can be administered, e.g., in the form as marketed, e.g. under the trademark Cinnarizin forte-ratiopharm™. Nimodipine can be administered, e.g., in the form as marketed, e.g. under the trademark Nimotop™. Donepezil hydrochloride can be administered, e.g., in the form as marketed, e.g. under the trademark Aricept™. Rivastigmine can be prepared as disclosed in U.S. Pat. No. 5,602,176. It can be administered, e.g., in the form as marketed, e.g. under the trademark Exelon™. Galantamine hydrobromide can be administered, e.g., in the form as marketed, e.g. under the trademark Reminyl™. Dihydroergotoxin can be administered, e.g., in the form as marketed, e.g. under the trademark Hydergin™. Nicergoline can be administered, e.g., in the form as marketed, e.g. under the trademark Sermion™. Piracetam can be administered, e.g., in the form as marketed, e.g. under the trademark Cerebroforte™. Pentifyllin can be administered, e.g., in the form as marketed, e.g. under the trademark Cosaldon™. Pyritinol can be administered, e.g., in the form as marketed, e.g. under the trademark Encephabol™. Vinpocetin can be administered, e.g., in the form as marketed, e.g. under the trademark Cavinton™. Memantine can be administered, e.g., in the form as marketed, e.g. under the trademarks Axura™ or Namenda™.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

Hence, the present invention pertains also to a combination comprising a CONSTRUCT of the invention, and at least one nootropic agent selected from the group consisting of nootropic plant extracts, calcium antagonists, cholinesterase inhibitors, dihydroergotoxin, nicergoline, piracetame, purine derivates, pyritinol, vincamine and vinpocetine or memantine, in which the active ingredients are present in each case in free form or in the form of a pharmaceutically acceptable salt and optionally at least one pharmaceutically acceptable carrier, for simultaneous, separate or sequential use, especially for use in a method of treating dementia.

Such a combination is preferably a combined preparation.

Other agents can be used in combination with the CONSTRUCT, for example: antidepressants such as SSRIs, SNRIs, NRIs, antipsychotics such as risperidone, antidiabetic treatments such as insulin or metformin, antioxidative treatments such as selegiline, vitamin E, anti-inflammatory treatments such as NSAIDs, lipid-lowering agents such as statins, hormone substitution such as estrogens, amyloid lowering agents such as abeta secretase inhibitors, aggregation inhibitors such as beta-sheet blockers, chelators, immunomodulatory agents such as glatiramer acetate.

The term "a combined preparation", as used herein defines especially a "kit of parts" in the sense that the active ingredients as defined above can be dosed independently or by use of different fixed combinations with distinguished amounts of the ingredients, i.e., simultaneously or at different time points. The parts of the kit can then, e.g., be administered simultaneously or chronologically staggered, that is at different time points and with equal or different time intervals for any part of the kit of parts. Preferably, the time intervals are chosen such that the effect on the treated disease in the combined use of the parts is larger than the effect which would be obtained by use of only any one of the active ingredients.

Hence, the present invention also provides
   the use of a combination as disclosed herein for the preparation of a medicament for the treatment of dementia, in particular Alzheimer's disease; and
   a commercial package comprising a combination as disclosed herein together with instructions for simultaneous, separate or sequential use thereof in the treatment of dementia, in particular Alzheimer's disease.

In one preferred embodiment of the invention, the combination partner (b) is a cholinesterase inhibitor, especially rivastigmine, or memantine.

If the combination partners are administered as separate dosing forms, a dosage and mode of administration can be applied as provided in the package inserts. In particular, the following dosages of the combination partners (b) can be administered to the patient:

Cinnarizine may be administered to a patient in a total daily dosage of between about 75 to about 150 mg.

Nimodipine may be administered to a patient in a total daily dosage of between about 60 to about 120 mg.

Donepezil hydrochloride may be administered to a patient in a total daily dosage of between about 5 mg and 10 mg.

Rivastigmine may be administered to a patient in a total daily dosage of between about 6 and about 12 mg.

Galantamine may be administered to a patient in a total daily dosage of between about 12 and 24 mg, e.g. 12 mg twice daily.

Dihydroergotoxin may be administered in the form of its methansulfonate to a patient in a total daily dosage of between about 4 mg and 10 mg, e.g. about 8 mg.

Nicergoline may be administered in the form of its tartrate by intramuscular injection to a patient in a total daily dosage of between about 4 mg and 8 mg.

Piracetam may be administered to a patient in a total daily dosage of between about 1200 and 5000 mg, e.g. 4800 mg/day.

Pentifyllin may be administered to a patient in a total daily dosage of between about 400 and 800 mg.

Pyritinol may be administered in the form of its hydrochloride to a patient in a total daily dosage of about 600 mg.

Vinpocetin may be administered to a patient in a total daily dosage of between about 10 and 15 mg.

Memantine may be administered to a patient in the form of memantine hydrochloride in a total daily dosage of about 20 mg.

In a further aspect, the present invention provides human monoclonal antibodies against Aβ1-42 induced by the CONSTRUCT, preferably Aβ antibodies recognizing the N-terminus of Aβ1-42.

An efficient method to make human monoclonal antibodies from B cells isolated from the blood of a human patient is described by Elisabetta Traggiai, Stephan Becker, Kanta Subbarao, Larissa Kolesnikova, Yasushi Uematsu, Maria Rita Gismondo, Brian R Murphy, Rino Rappuoli & Antonio Lanzavecchia in *Nature Medicine* 10, 871-875 (2004), which publication is included by reference into the present specification.

EXAMPLES

In the following Examples 1 to 4, male and female patients are included aged between 50 to 80 years (both inclusive), with mild to moderate AD as confirmed by a MMSE score of 16 to 26 (both inclusive), who are outpatients with caregivers (living together or, if living alone, with daily contact), who meet the DSM-IV criteria for dementia of the Alzheimer's type, and who satisfy the criteria for a clinical diagnosis of probable AD according to the National Institute of Neurological and Communicative Disorders and Stroke (NINCDS-ADRDA). Each patient participates in a 4-week screening period (Day -28 to Day -1), a baseline period (pre-dose on Day 1 in week 0), three single dose treatments under ambulatory conditions in weeks 0, 6 and 18 (Days 1, 43, 127), ten additional ambulatory visits in bi- to four weekly intervals in weeks 2, 4, 8, 12, 16, 20, 22, 26, 30, and 34 (i.e. on Study Days 15, 29, 57, 85, 113, 141, 155, 183, 211 and 239), and two additional ambulatory visits in week 42 and 52 (i.e. on Study Days 295 and 365). Safety assessments include general physical examinations, neurological examinations, 12-lead electrocardiograms (ECGs), vital signs, standard clinical laboratory evaluations (hematology, blood chemistry, urinalysis), special immunological laboratory evaluations in blood and cerebrospinal fluid (CSF), cerebral magnetic resonance imagings (MRIs), as well as adverse event and serious adverse event monitoring. Further, patients and caregivers are instructed (verbally and in writing) to look for any unexpected deterioration in health status.

Aβ-antibody response is measured by determination of the Aβ-antibody titer (IgG and IgM) in serum and CSF using ELISA methods. The ex vivo Aβ-antibody binding properties in serum and CSF is explored by immunological methods on human and β-amyloid precursor protein (APP) transgenic mouse brain tissue. The VLP-antibody titer response in serum is measured to investigate the immune response to the carrier compound in relation to the immune response to Aβ.

Exploratory pharmacodynamic assessments include the following assessments: 1) determination of disease related markers in CSF (Aβ peptides and its isoforms, tau protein and its isoforms, phospho-tau) and plasma (Aβ peptides and isoforms); 2) volumetric MRIs, and 3) neuropsychological test battery, mini-mental state examination (MMSE), clinical dementia rating (CDR) and Alzheimer's Disease Cooperative Study—Activities of Daily Living (ADCS-ADL), 4) Positron emission tomography (PET) with $^{11}$C-Pittsburgh Compound-B ($^{11}$C-PIB) which is a novel beta-amyloid selective tracer developed for in vivo detection of β-amyloid plaques in the brain and $^{18}$F-fluorodeoxyglucose ($^{18}$FDG)

Responders are defined as those patients who show a significant increase of Aβ-specific antibody titers above baseline and who show an antibody isotype switch from IgM to IgG in serum at latest after the 3rd injection. Aβ-specific antibody titers are defined as titers above lower limit of quantification (LLOQ) in a validated enzyme-linked immunosorbent assay (ELISA) assay detecting specific antibodies relative to a standard serum as calibrator.

Example 1

A Single or Multi Center, Randomized, Double-blind, Placebo-controlled Study in Patients with Mild to Moderate Alzheimer's Disease (AD) with Three Subcutaneous Injections of 25 µg of CONSTRUCT A total of 30 patients is randomized to receive three s.c. injections of the CONSTRUCT or placebo. 24 patients receive the active drug CONSTRUCT and 6 patients receive placebo under double-blind conditions. Three s.c. injections of 25 µg CONSTRUCT or placebo are administered to each patient in weeks 0, 6 and 18.

Example 2

A Single or Multicenter, Randomized, Double-blind, Placebo-controlled Study in Patients with Mild to Moderate Alzheimer's Disease (AD) with Three Subcutaneous Injections of 50 µg of CONSTRUCT A total of 30 patients is randomized to receive three s.c. injections of the CONSTRUCT or placebo. 24 patients receive the active drug CONSTRUCT and 6 patients receive placebo under double-blind conditions. Three s.c. injections of 50 µg CONSTRUCT or placebo are administered to each patient in weeks 0, 6 and 18.

Example 3

A Single or Multicenter, Randomized, Double-blind, Placebo-controlled Study in Patients with Mild to Moderate Alzheimer's Disease (AD) with Three Subcutaneous Injections of 100 µg of CONSTRUCT A total of 30 patients is randomized to receive three s.c. injections of the CONSTRUCT or placebo. 24 patients receive the active drug CONSTRUCT and 6 patients receive placebo under double-blind conditions. Three s.c. injections of 100 µg CONSTRUCT or placebo are administered to each patient in weeks 0, 6 and 18.

Example 4

Determination of Antibody Titers in Serum

Blood samples are taken by direct venipuncture. A total of 10 mL venous blood is collected in plain barrier tubes. The sample are allowed to clot during 45 minutes at room temperature and then centrifuged for 10 minutes at approximately 2500 g. Serum tubes are frozen within 60 min after venipuncture and kept at <−70° C. pending analysis.

Example 5

A Single or Multicenter, Randomized, Double-blind, Placebo-controlled Study in Patients with Mild to Moderate Alzheimer's Disease (AD) with Three Subcutaneous Injections of 150 µg of CONSTRUCT A total of 30 patients is randomized to receive three s.c. injections of the CONSTRUCT or placebo. 24 patients receive the active drug CONSTRUCT and 6 patients receive placebo under double-blind conditions. Three s.c. injections of 150 µg CONSTRUCT or placebo are administered to each patient in weeks 0, 6 and 18.

Example 6

A Single or Multicenter, Randomized, Double-blind, Placebo-controlled Study in Patients with Mild to Moderate Alzheimer's Disease (AD) with Three Subcutaneous Injections of 300 µg of CONSTRUCT A total of 30 patients is randomized to receive three s.c. injections of the CONSTRUCT or placebo. 24 patients receive the active drug CONSTRUCT and 6 patients receive placebo under double-blind conditions. Three s.c. injections of 300 µg CONSTRUCT or placebo are administered to each patient in weeks 0, 6 and 18.

What is claimed is:

1. A method of treatment of dementia in human patients comprising administering a construct consisting of a virus-like particle (VLP) structure chemically coupled to a fragment of the Aβ-1-42 peptide or its pharmaceutically acceptable salts, characterized in that the construct is administered subcutaneously.

2. The method according to claim 1 wherein the dementia is dementia of the Alzheimer's type or vascular dementia with amyloid angiopathy.

3. The method according to claim 1 wherein the patients are at risk of developing Alzheimer's Disease, and further wherein the patients are selected from the group consisting of patients with mild cognitive impairment, patients with genotypes known to be associated with Alzheimer's Disease, patients with Trisomy 21 and patients with surrogate markers indicating risk for Alzheimer's Disease.

4. The method according to claim 1 wherein the construct is administered at a total dose between about 5 to 300 µg every 4 to 8 weeks.

5. The method according to claim 1 wherein the construct is administered at a total dose between about 5 to 175 µg every 4 to 8 weeks.

6. The method according to claim 1 wherein the construct consists of capsid proteins of a RNA bacteriophage self-assembled into a highly ordered VLP structure chemically coupled with a bivalent linker to a fragment of the Aβ1-42 peptide.

7. The method according to claim 6 wherein the capsid proteins are taken from the RNA bacteriophage Qβ.

8. The method according to claim 6 wherein the fragment of the Aβ1-42 peptide is Aβ-1-6.

9. A method of treatment of dementia in human patients comprising administering 5 to 1000 µg of a construct consisting of a VLP structure chemically coupled to a fragment of the Aβ-1-42 peptide or its pharmaceutically acceptable salts to human patients in need thereof about every 4 to 8 weeks.

10. The method according to claim 1, wherein between 0.25 and 0.75 mg/mL. of said construct is administered subcutaneously, and further wherein said construct is in an aqueous solution further comprising phosphate buffer saline.

* * * * *